US006258778B1

(12) United States Patent
Rodgers et al.

(10) Patent No.: US 6,258,778 B1
(45) Date of Patent: Jul. 10, 2001

(54) METHODS FOR ACCELERATING BONE AND CARTILAGE GROWTH AND REPAIR

(75) Inventors: Kathleen E. Rodgers, Long Beach; Gere S. DiZerega, Pasedena, both of CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/352,191

(22) Filed: Jul. 12, 1999

Related U.S. Application Data

(60) Provisional application No. 60/130,855, filed on Apr. 22, 1999, and provisional application No. 60/092,653, filed on Jul. 13, 1998.

(51) Int. Cl.[7] .......................... A61K 38/00; A01N 37/18; C07K 5/00; C07K 7/00

(52) U.S. Cl. ................................ 514/2; 514/12; 514/21; 530/300; 530/324; 424/185.1

(58) Field of Search ..................... 514/412, 21; 530/300, 530/324; 424/185.1

(56) References Cited

U.S. PATENT DOCUMENTS

| | | |
|---|---|---|
| 4,642,120 | 2/1987 | Nevo et al. . |
| 5,013,649 | 5/1991 | Wang et al. . |
| 5,015,629 | 5/1991 | diZerega . |
| 5,053,050 | 10/1991 | Itay . |
| 5,171,273 | 12/1992 | Silver et al. . |
| 5,324,775 | 6/1994 | Rhee et al. . |
| 5,443,515 | 8/1995 | Cohen et al. . |
| 5,464,439 | 11/1995 | El Gendler . |
| 5,607,474 | 3/1997 | Athanasiou et al. . |
| 5,629,292 | 5/1997 | Rodgers et al. . |
| 5,656,598 | 8/1997 | Dunstan et al. . |
| 5,686,116 | 11/1997 | Bockman et al. . |
| 5,693,616 | 12/1997 | Krstenansky et al. . |
| 5,700,774 | 12/1997 | Hattersley et al. . |
| 5,716,935 | 2/1998 | Rodgers et al. . |
| 5,736,372 | 4/1998 | Vacanti et al. . |
| 5,834,432 | 11/1998 | Rodgers et al. . |
| 5,916,207 | 6/1999 | Toyoda . |
| 5,955,430 | 9/1999 | Rodgers et al. . |

FOREIGN PATENT DOCUMENTS

| | | |
|---|---|---|
| WO 88/00205 | 1/1988 | (WO) . |
| WO 95/08337 | 3/1995 | (WO) . |
| WO 95/08565 | 3/1995 | (WO) . |
| WO 96/14858 | 5/1996 | (WO) . |
| WO 96/15795 | 5/1996 | (WO) . |
| WO 96/39164 | 12/1996 | (WO) . |
| WO 96/40090 | 12/1996 | (WO) . |
| WO 98/26795 | 6/1998 | (WO) . |
| WO 98/32457 | 7/1998 | (WO) . |
| WO 98/33813 | 8/1998 | (WO) . |
| WO 99/26644 | 6/1999 | (WO) . |
| WO 99/31125 | 6/1999 | (WO) . |
| WO 99/46285 | 9/1999 | (WO) . |

OTHER PUBLICATIONS

Okazaki, et al., (1996), Ann. Rheum. Dis., 55: pp. 181–186.
Price, et al., (1982), Proc. Natl. Acad. Sci. USA, 79: pp. 7734–7738.
Georgescu, et al., (1988), In Vitro Cell. Dev. Biol., 24: pp. 1015–1022.
Kream, et al., (1985), Endocrinol., 116: pp. 296–302.
Lowry, et al., (1954), J. Biol. Chem., 207: pp. 19–37.
Kato, et al., (1985), J. Cell Biol., 100: pp. 477–485.
Hatton, et al., (1977), J. of Endocrinol., 152: pp. 5–10.
Lamparter, et al., (1998), Physiol., 175: pp. 89–98.
Hiruma, et al., (1997), Biochem and Biophys. Res. Commun., 230: pp. 176–178.
Hagiwara, et al., (1998), J. Of Endocrinology, 156: pp. 543–550.
Speth and Kim, (1990), BBRC, 169: pp. 997–1006.
Catalioto, et al., (1994), Eur. J. Pharmacol., 256: pp. 93–97.
Bryson, et al., (1992), Eur. J. Pharmacol., 225: pp. 119–127.
Janiak, et al., (1992), Hypertension, 20: pp. 737–745.
Prescott, et al., (1991), Am. J. Pathol., 139: pp. 1291–1295.
Kauffman, et al., (1991), Life Sci., 49: pp. 223–228.
Viswanathan, et al., (1992), Peptides, 13: pp. 783–786.
Kimura, et al., (1992), BBRC, 187: pp. 1083–1090.
Pfeilschifter, et al., (1992), Eur. J. Pharmacol., 225: pp. 57–62.
Jaiswal, et al., (1992), Hypertension 19(Supp. II): II–49–II–55.
Edwards and Stack, (1993), J. Pharmacol. Exper. Ther., 266: pp. 506–510.
Jaiswal, et al., (1993), J. Pharmacol. Exper. Ther., 265: pp. 664–673.
Jaiswal, et al., (1991), Hypertension, 17: pp. 1115–1119.
Portsi, et al., (1994), Br. J. Pharmacol., 111: pp. 652–654.
Regoli, et al., (1974), Pharmacological Reviews, 26: pp. 69–123.
Clouston, et al., (1988), Genomics, 2: pp. 240–248.
Kageyama, et al., (1984), Biochemistry, 23: pp. 3603–3609.
Ohkubo, et al., (1983), Proc. Natl. Acad. Sci., 80: pp. 2196–2200.
Dzau, et al., (1989), J. Mol. Cell. Cardiol., 21: S7 (Supp III).
Berk, et al., (1989), Hypertension, 13: pp. 305–314.
Kawahara, et al., (1988), BBRC, 150P pp. 52–59.
Naftilan, et al., (1989), J. Clin. Invest., 83: pp. 1419–1423.
Taubman, et al., (1989), J. Bio. Chem., 264: 526–530.

(List continued on next page.)

*Primary Examiner*—Avis M. Davenport
(74) *Attorney, Agent, or Firm*—McDonnell, Boehnen, Hulbert & Berghoff; David S. Harper

(57) ABSTRACT

The present invention provides improved methods, kits, and compositions for enhancing bone, cartilage and cartilage repair, bone and prosthesis implantation, and attachment and fixation of cartilage and cartilage to bone or other tissues, and chondrocyte proliferation comprising the administration of an effective amount of angiotensinogen, angiotensin I (AI), AI analogues, AI fragments and analogues thereof, angiotensin II (AII), AII analogues, AII fragments or analogues thereof or AII $AT_2$ type 2 receptor agonists.

35 Claims, 4 Drawing Sheets

OTHER PUBLICATIONS

Nakahara, et al., (1992), BBRC, 184: pp. 811–818.
Stouffer and Owens, (1992), Circ. Res., 70: p. 820–828.
Wolf, et al., (1992), Am. J. Pathol., 140: pp. 95–107.
Bell and Madri, et al., (1990), Am. J. Pathol., 137: pp. 7–12.
Fernandez, et al., (1985), J. Lab. Clin. Med., 105: p. 141–145.
LeNoble, et al., (1991), Eur. J. Pharmacol., 195: pp. 305–306.
Slovik, et al., (1986), J. Bone & Min. Res., 1: pp. 377–381.
Toriumi, et al., (1991), Arch. Otolaryngol Head Neck Surg., 117: pp. 1101–1112.
Gerhart, et al., (1991), Trans Orthop Res Soc., 16: p. 172.
Wozney, et al., (1993), Bone Morphogenetic Proteins and Their Gene Expression, in Cellular and Molecular Biology of Bone, (Academic Press, Inc.), pp. 131–167.
Wozney, et al., (1988), Science, 242: pp. 1528–1534.
Sporn, et al., (1987), J. Cell. Biol., 105: pp. 1039–1045.
Centrella, et al., (1987), J. Biol. Chem., 262: pp. 2869–2874.
Chenu, et al., (1988), Proc. Natl. Acad. Sci. U.S.A., 85: pp. 5683–5687.
Kiebzak, et al., (1988), J. Bone Min. Res., 3: pp. 439–446.
Joyce, et al., (1990), J. Cell. Biol., 110: pp. 2195–2207.
Noda and Camilliere, (1989), Endocrinology, 124: pp. 2991–2994.
Dijke, et al., Bio/Technology, (1989), 7: pp. 793–798.
Hagiwara, et al., (1998), "Regulation of bone metabolism by vasoactive peptides" Saishin Igaku, vol.: 53 (6) pp. 1289–1294 (Translated from Japanese).

SEQUENCE LISTING

```
<160> NUMBER OF SEQ ID NOS: 45

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:AII

<400> SEQUENCE: 1

Asp Arg Val Tyr Ile His Pro Phe
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:AII (2-8)

<400> SEQUENCE: 2

Arg Val Tyr Ile His Pro Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:AII (3-8)

<400> SEQUENCE: 3

Val Tyr Ile His Pro Phe
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:AII (1-7)

<400> SEQUENCE: 4

Asp Arg Val Tyr Ile His Pro
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:AII (2-7)

<400> SEQUENCE: 5

Arg Val Tyr Ile His Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:AII (3-7)

<400> SEQUENCE: 6
```

```
Val Tyr Ile His Pro
  1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:AII (5-8)

<400> SEQUENCE: 7

Ile His Pro Phe
  1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:AII (1-6)

<400> SEQUENCE: 8

Asp Arg Val Tyr Ile His
  1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:AII (1-5)

<400> SEQUENCE: 9

Asp Arg Val Tyr Ile
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:AII (1-4)

<400> SEQUENCE: 10

Asp Arg Val Tyr
  1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:AII (1-3)

<400> SEQUENCE: 11

Asp Arg Val
  1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (2)
<223> OTHER INFORMATION: Nle
```

```
<400> SEQUENCE: 12

Arg Xaa Tyr Ile His Pro Phe
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (4)
<223> OTHER INFORMATION: Nle

<400> SEQUENCE: 13

Arg Val Tyr Xaa His Pro Phe
 1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence:AII (6-8)

<400> SEQUENCE: 14

His Pro Phe
 1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:AII (4-8)

<400> SEQUENCE: 15

Tyr Ile His Pro Phe
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:AII analogue
      class
<220> FEATURE:
<221> NAME/KEY: UNSURE
<222> LOCATION: (1)
<223> OTHER INFORMATION: Xaa at poistion 1 can be Arg, Lys, Ala, Orn,
      Ser, MeGly, D-Arg, or D-Lys
<220> FEATURE:
<221> NAME/KEY: UNSURE
<222> LOCATION: (2)
<223> OTHER INFORMATION: Xaa at position 2 can be Val, Ala, Leu, Nle,
      Ile, Gly, Pro, Aib, Acp, or Tyr
<220> FEATURE:
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
 1               5
```

```
<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 17

Arg Val Tyr Gly His Pro Phe
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 18

Arg Val Tyr Ala His Pro Phe
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:AII analogue
      1

<400> SEQUENCE: 19

Asp Arg Val Tyr Val His Pro Phe
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:AII analogue
      2

<400> SEQUENCE: 20

Asn Arg Val Tyr Val His Pro Phe
 1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:AII analogue
      3

<400> SEQUENCE: 21

Ala Pro Gly Asp Arg Ile Tyr Val His Pro Phe
 1               5                  10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:AII analogue
      4

<400> SEQUENCE: 22

Glu Arg Val Tyr Ile His Pro Phe
```

```
                                1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:AII analogue
      5

<400> SEQUENCE: 23

Asp Lys Val Tyr Ile His Pro Phe
  1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:AII analogue
      6

<400> SEQUENCE: 24

Asp Arg Ala Tyr Ile His Pro Phe
  1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:AII analogue
      7

<400> SEQUENCE: 25

Asp Arg Val Thr Ile His Pro Phe
  1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:AII analogue
      8

<400> SEQUENCE: 26

Asp Arg Val Tyr Leu His Pro Phe
  1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:AII analogue
      9

<400> SEQUENCE: 27

Asp Arg Val Tyr Ile Arg Pro Phe
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:AII analogue
```

```
                         10

<400> SEQUENCE: 28

Asp Arg Val Tyr Ile His Ala Phe
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:AII analogue
      11

<400> SEQUENCE: 29

Asp Arg Val Tyr Ile His Pro Tyr
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:AII analogue
      12

<400> SEQUENCE: 30

Pro Arg Val Tyr Ile His Pro Phe
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:AII analogue
      13

<400> SEQUENCE: 31

Asp Arg Pro Tyr Ile His Pro Phe
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:AII analogue
      14
<220> FEATURE:
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:AII analogue
      15
<220> FEATURE:
<221> NAME/KEY: MOD_RES
<222> LOCATION: (3)
<223> OTHER INFORMATION: Nle
```

<400> SEQUENCE: 33

Asp Arg Xaa Tyr Ile His Pro Phe
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:AII analogue
      16
<220> FEATURE:
<221> NAME/KEY: MOD_RES
<222> LOCATION: (5)
<223> OTHER INFORMATION: Nle

<400> SEQUENCE: 34

Asp Arg Val Tyr Xaa His Pro Phe
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:AII analogue
      17
<220> FEATURE:
<221> NAME/KEY: MOD_RES
<222> LOCATION: (4)
<223> OTHER INFORMATION: homo Ser

<400> SEQUENCE: 35

Asp Arg Val Ser Tyr Ile His Pro Phe
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial
      Sequence:p-aminophenylalanine 6 AII
<220> FEATURE:
<221> NAME/KEY: MOD_RES
<222> LOCATION: (6)
<223> OTHER INFORMATION: p-aminophenylalanine

<400> SEQUENCE: 36

Asp Arg Val Tyr Ile Xaa Pro Phe
1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:angiotensin
      I

<400> SEQUENCE: 37

Asp Arg Val Tyr Ile His Pro Phe His Leu
1               5                   10

<210> SEQ ID NO 38
<211> LENGTH: 8
<212> TYPE: PRT
<213> ORGANISM: Artificial Sequence

```
<220> FEATURE:
<221> NAME/KEY: MOD_RES
<222> LOCATION: (2)
<223> OTHER INFORMATION: Orn
<220> FEATURE:
<223> OTHER INFORMATION: Description of Artificial Sequence:GSD37B:
      Orn2-AII

<400> SEQUENCE: 38

Asp Xaa Val Tyr Ile His Pro Phe
 1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence:GSD28:
      Ile8-AII

<400> SEQUENCE: 39

Asp Arg Val Tyr Ile His Pro Ile
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:1GD:
      Ala4-AII(1-7)

<400> SEQUENCE: 40

Asp Arg Val Ala Ile His Pro
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:2GD:
      Pro3-AII(1-7)

<400> SEQUENCE: 41

Asp Arg Pro Tyr Ile His Pro
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:Gly1-AII

<400> SEQUENCE: 42

Gly Arg Val Tyr Ile His Pro Phe
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial
      Sequence:GSD38B:Citron2-AII
<220> FEATURE:
<221> NAME/KEY: MOD_RES
<222> LOCATION: (2)
```

```
-continued

<223> OTHER INFORMATION: Citron

<400> SEQUENCE: 43

Asp Xaa Val Tyr Ile His Pro Phe
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial
      Sequence:Pro3Ala4-AII(1-7)

<400> SEQUENCE: 44

Asp Arg Pro Ala Ile His Pro
 1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence:9GD:
      norleu3-AII(1-7)
<220> FEATURE:
<221> NAME/KEY: MOD_RES
<222> LOCATION: (3)
<223> OTHER INFORMATION: Nle

<400> SEQUENCE: 45

Asp Arg Xaa Tyr Ile His Pro
 1               5
```

METHODS FOR ACCELERATING BONE AND CARTILAGE GROWTH AND REPAIR

CROSS REFERENCE

This application is a continuation-in-part of U.S. Provisional application Ser. No. 60/092,653 filed Jul. 13, 1998 and a continuation in part of U.S. Provisional application Ser. No. 60/130,855 filed Apr. 22, 1999.

FIELD OF THE INVENTION

The present invention relates to methods, compositions, and kits for the repair, regeneration, and implantation of bone and cartilage.

BACKGROUND OF THE INVENTION

Natural mechanisms of repair, healing and augmentation are similar for bone and cartilage. (U.S. Pat. No. 5,686,116) Although repair, healing and augmentation require a complex series of events that are not well defined, it is known that specific, naturally occurring factors are required to achieve these objectives. Such factors are released or migrate into the injured area, and stimulate osteoblasts and chondrocytes and odontoblasts in bone and cartilage to stimulate matrix formation and remodeling of the wounded area. (ten Dijke et al., Bio/Technology, 7:793–798 (1989))

Living bone tissue is continuously being replenished by the processes of resorption and deposition of bone matrix and minerals. This temporally and spatially coupled process, termed bone remodeling, is accomplished largely by two cell populations, the osteoclasts and osteoblasts. (U.S. Pat. No. 5,656,598, incorporated by reference herein in its entirety) The remodeling process is initiated when osteoclasts are recruited from the bone marrow or the circulation to the bone surface and remove a disk-shaped packet of bone. The bone matrix and mineral is subsequently replaced by a team of osteoblasts recruited to the resorbed bone surface from the bone marrow. Osteoblasts are derived from local mesenchymal (stromal) precursors which differentiate into osteoblasts.

New bone can be formed by three basic mechanisms: osteogenesis, osteoconduction and osteoinduction. (U.S. Pat. No. 5,464,439 incorporated by reference herein in its entirety) In osteogenic transplantation, viable osteoblasts and peri-osteoblasts are moved from one body location to another where they establish centers of bone formation. Cancellous bone and marrow grafts provide such viable cells. TGF-beta has been shown to stimulate proliferation and matrix synthesis of osteoblastic cells (Centrella, et al. (1987) J. Biol. Chem. 262:2869–2874) and to inhibit the formation and activity of osteoclastic cells (Chenu, et al. (1988) Proc. Natl. Acad. Sci. U.S.A. 85:683–5687; Kiebzak et al. (1988) J. Bone Min. Res. 3:439–446), and to stimulate local bone formation in vivo. (Joyce, et al. (1990) J. Cell. Biol. 110:2195–2207; Noda and Camilliere (1989) Endocrinology 124:2991–2294). Other factors reported to stimulate bone growth include bone morphogenetic proteins (WO 88/00205), insulin-like growth factor (IGF) (Endocrinol. Metab. 13:E367–72,1986), and parathyroid hormone (J. Bone & Min. Res. 1:377–381, 1986).

Members of the bone morphogenetic protein family have been shown to be useful for induction of cartilage and bone formation. For example, BMP-2 has been shown to be able to induce the formation of new cartilage and/or bone tissue in vivo in a rat ectopic implant model, see U.S. Pat. No. 5,013,649; in mandibular defects in dogs, see Toriumi et al., Arch. Otolaryngol Head Neck Surg., 117:1101–1112 (1991); and in femoral segmental defects in sheep, see Gerhart et al., Trans Orthop Res Soc, 16:172 (1991). Other members of the BMP family have also been shown to have osteogenic activity, including BMP-4, -6 and -7 (see Wozney, Bone Morphogenetic Proteins and Their Gene Expression, in Cellular and Molecular Biology of Bone, pp. 131–167 (Academic Press, Inc. 1993)). BMP proteins have also been shown to demonstrate inductive and/or differentiation potentiating activity on a variety of other tissues, including cartilage. (U.S. Pat. No. 5,700,774, hereby incorporated by reference in its entirety.

In the transplantation of large segments of cortical bone or allogenic banked bone, direct osteogenesis does not occur. Rather, osteoconduction occurs wherein the dead bone acts as a scaffold for the ingrowth of blood vessels, followed by the resorption of the implant and deposition of new bone. This process is very slow however, often requiring years to reunite a large segmental defect.

Osteoinduction is the phenotypic conversion of connective tissue into bone by an appropriate stimulus. As this concept implies, formation of bone can be induced at even non-skeletal sites. Osteoinduction is preferred over osteoconduction, as grafts of this type are typically incorporated into the host bone within a two-week period. In contrast, osteoconductive grafts have been found to be non-incorporated as long as one year after implantation. In order to provide an environment suitable for osteoinduction, a material should be selected which is not only capable of inducing osteogenesis throughout its volume, but is also biocompatible, non-inflammatory, and possesses the ability to be ultimately resorbed by the body and replaced with new, natural bone.

Among the pathological conditions associated with abnormal bone cell function are osteoporosis, osteoarthritis, Paget's disease, osteohalisteresis, osteomalacia, periodontal disease, bone loss resulting from multiple myeloma and other forms of cancer, bone loss resulting from side effects of other medical treatment (such as steroids), and age-related loss of bone mass. Inadequate organic matrix mass places an individual at risk of skeletal failure such that bone fractures can result from the minimal trauma of everyday life. Such fractures cause significant illness, or morbidity, inasmuch as there is insufficient repair or healing of the fractures. In certain pathologic conditions, osteoclast-mediated resorption is not regulated by osteoblasts but is driven by cancer cells, infecting organisms or the host's immune cells. In those disease conditions, resorption of bone far exceeds bone formation. Such accelerated osteoclastic activity leads to excessive release of calcium from the inorganic mineral in bone, with a concomitant net loss of skeletal mass, often with an attendant disturbance in calcium homeostasis in the form of elevated blood levels of calcium. (U.S. Pat. No. 5,686,116, incorporated by reference herein in its entirety.)

Although methods for directing new bone formation are known, improved methods that provide for accelerated bone growth are needed. For example, currently approved therapeutic agents for osteoporosis are antiresorptives. As such, they are not as effective in patients with established osteoporosis of either type (decreased bone density with fractures of the vertebrae and/or hip), or in patients with Type II osteoporosis. In addition, the most accepted preventive agent for osteoporosis currently in use is estrogen therapy, which is not an acceptable therapeutic agent for women with a history of breast cancer or endometrial cancer or for men with osteoporosis.

Similarly, successful implantation and function of bone implants depends on bonding of the adjacent bone to the implant. (U.S. Pat. No. 5,686,116) Such bonding requires bone repair by the formation of new matrix components at the interface between the implant and the bone proximate to the implant. An estimated ten percent of bone and joint prosthetic devices that are placed in people fail to function due to non-bonding of the bone to an implant. The resulting disability often requires reoperation and reimplantation of the device. Furthermore, five to ten percent of all bone fractures are never repaired. Although many methods have been proposed to cure these non-healing bone fractures, none has yet proven to be satisfactory. Based on all of the above, there clearly exists a need in the art for improved methods that provide for accelerated bone growth.

Cartilage is a specialized type of dense connective tissue consisting of cells embedded in a matrix. There are several kinds of cartilage. (U.S. Pat. No. 5,736,372, herein incorporated by reference in its entirety.) Translucent cartilage having a homogeneous matrix containing collagenous fibers is found in articular cartilage, in costal cartilages, in the septum of the nose, in larynx and trachea. Articular cartilage is hyaline cartilage covering the articular surfaces of bones. Costal cartilage connects the true ribs and the sternum. Fibrous cartilage contains collagen fibers. Yellow cartilage is a network of elastic fibers holding cartilage cells which is primarily found in the epiglottis, the external ear, and the auditory tube. Cartilage is tissue made up of extracellular matrix primarily comprised of the organic compounds collagen, hyaluronic acid (a proteoglycan), and chondrocyte cells, which are responsible for cartilage production. Collagen, hyaluronic acid and water entrapped within these organic matrix elements yield the unique elastic properties and strength of cartilage. Chondrocytes produce both Type I and Type II collagens. Type II collagen is not found in bone, whereas Type I collagen is found in bone. (U.S. Pat. No. 5,686,116) It has previously been shown that the endogenous growth factors TGF beta and BMP induce both new cartilage and bone formation. Wozney et al. Science, 242:1528–1533 (1988) and Sporn et al. J. Cell Biol. 105:1039–1045 (1987).

In cartilage, collagen synthesis is required for repair, healing and augmentation, as well as for the successful bonding of grafts and prosthetic devices. (U.S. Pat. No. 5,686,116) Collagen is the major structural protein responsible for the architectural integrity of cartilage. Thus, an adequate supply of chondrocytes is essential in order to produce sufficient amounts of collagen for repair, healing, and augmentation of cartilage. Other, noncollagen proteins, such as osteonectin, fibronectin and proteoglycans are also important for cartilage repair.

Cells such as synoviocytes that are found in joint spaces adjacent to cartilage have an important role in cartilage metabolism. Synoviocytes produce metallo-proteinases, such as collagenases that are capable of breaking-down cartilage. TGF beta is known to inhibit cell-release (and probably synthesis) of metallo-proteinases and to induce chondrocytes (cartilage forming cells) to produce new matrix components and inhibit production of cartilage destructive enzymes so as to effect cartilage repair, healing and augmentation. Spom et al. (1987). It has also been shown that mice deficient in parathyroid hormone-related peptide (PTHrP) exhibit abnormal cartilage maturation, indicating that PTHrP is an essential factor for chondrocyte development and maturation. (U.S. Pat. No. 5,700,774)

Cartilage implants are often used in reconstructive or plastic surgery such as rhinoplasty. There is a need in the art for methods that increase chondrocyte proliferation and collagen synthesis, and thus inhibit cartilage destruction and enhance cartilage repair. Such methods would increase the clinical utility of cartilage repair including but not limited to cartilage grafts and healing of cartilage grafts.

Although some of the above methods have met with limited success, there remains a need in the art for improved methods for enhancing bone and cartilage repair, healing and augmentation, and for enhancing the attachment and fixation of bone and cartilage implants.

SUMMARY OF THE INVENTION

The present invention provides methods, kits, and compositions for 1) enhancing bone and cartilage repair; 2) bone and prosthesis implantation; 3) attachment and fixation of cartilage to bone or other tissues; and methods, cell culture medium and kits for the proliferation of chondrocytes; all of which comprise the administration of angiotensinogen, angiotensin I (AI), AI analogues, AI fragments and analogues thereof, angiotensin II (AII), AII analogues, AII fragments or analogues thereof or AII $AT_2$ type 2 receptor agonists.

These aspects and other aspects of the invention become apparent in light of the following detailed description.

DETAILED DESCRIPTION OF THE PREFERRED EMBODIMENTS

Figure 1:
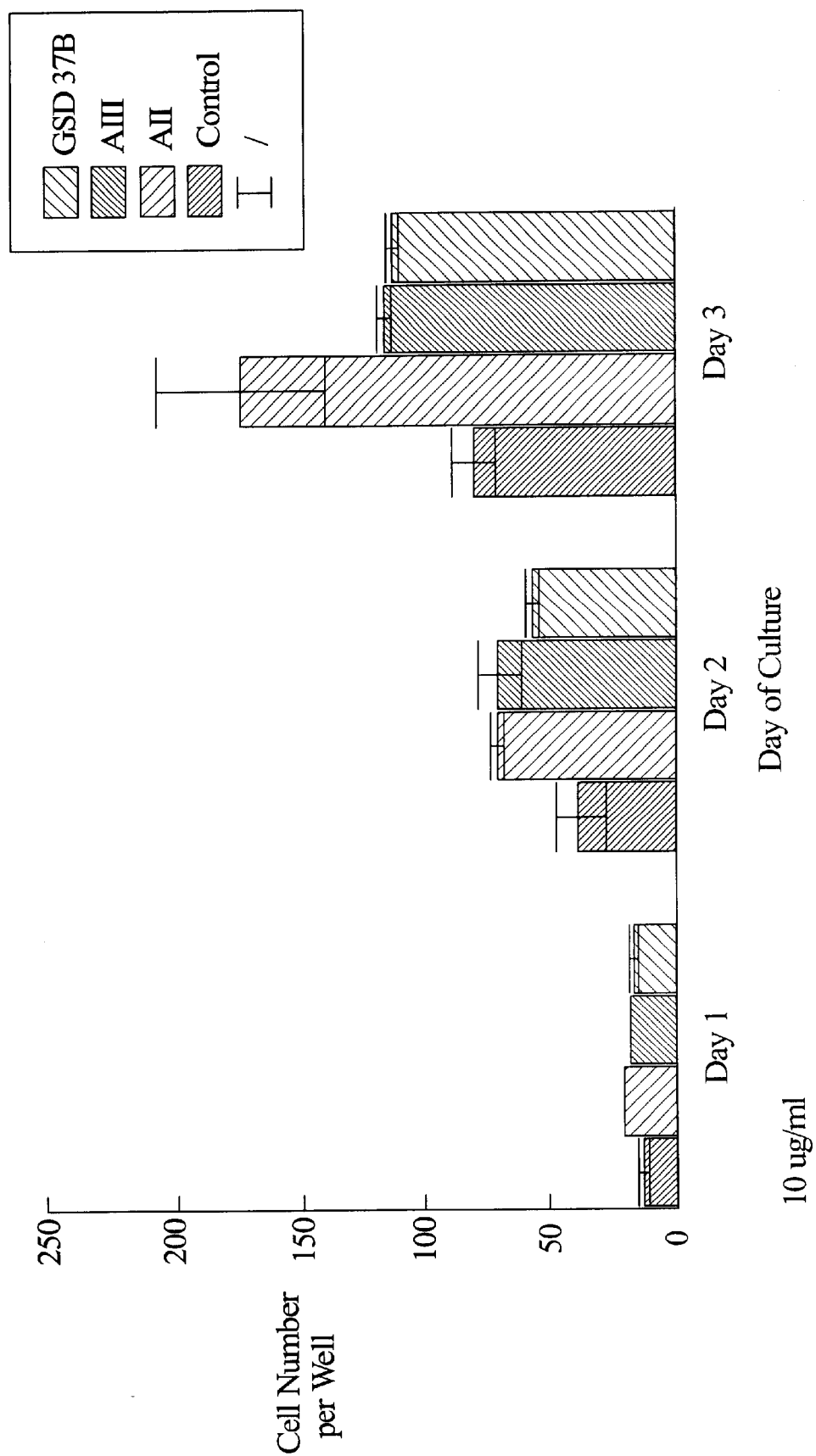
FIG. 1 is a bar graph showing the effect of AII, AIII, and GSD37B (10 μg/ml) on chondrocyte proliferation.

All references, patents and patent applications are hereby incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

As defined herein the phrase "enhancing bone repair" refers to increasing the rate of new bone formation via bone remodeling, osteogenesis, osteoconduction and/or osteoinduction. The methods for enhancing bone repair in a mammal of the invention include those that stimulate bone formation and those that reverse bone loss. The methods can thus be used for (1) providing a subject with an amount of a substance sufficient to act prophylactically to prevent the development of a weakened and/or unhealthy state; or (2) providing a subject with a sufficient amount of a substance so as to alleviate or eliminate a disease state and/or the symptoms of a disease state, and a weakened and/or unhealthy state.

As used herein the term "enhancing cartilage repair" comprises healing and regeneration of cartilage injuries, tears, deformities or defects, and prophylactic use in preventing damage to cartilaginous tissue.

The present invention fulfills the need for methods to enhance bone repair in a mammal suffering from bone fractures, defects, and disorders which result in weakened bones such as osteoporosis, osteoarthritis, Paget's disease, osteohalisteresis, osteomalacia, periodontal disease, bone loss resulting from multiple myeloma and other forms of cancer, bone loss resulting from side effects of other medical treatment (such as steroids), and age-related loss of bone mass. In addition, bony ingrowth into various prosthetic devices can be greatly enhanced so that such artificial parts are firmly and permanently anchored into the surrounding skeletal tissue through a natural osseous bridge.

The present invention further fulfills the need for methods to enhance the repair of cartilage in a mammal, by accelerating the proliferation of chondrocytes and thereby increasing the synthesis of collagen for use in cartilage repair. Such methods have application in the healing of cartilage, for example articular cartilage tears, deformities and other cartilage defects in humans and other animals. The methods have prophylactic use in preventing damage to cartilaginous tissue, as well as use in the improved fixation of cartilage to bone or other tissues and in repairing defects to cartilage tissue. De novo cartilaginous tissue formation induced by the compounds of the present invention contributes to the repair of congenital, trauma induced, or other cartilage defects of other origin, and is also useful in surgery for attachment or repair of cartilage. The methods and compositions of the invention may also be useful in the treatment of arthritis and other cartilage defects. The methods of the present invention can also be used in other indications wherein it is desirable to heal or regenerate cartilage tissue. Such indications include, without limitation, regeneration or repair of injuries to the articular cartilage. The methods of the present invention provide an environment to attract cartilage-forming cells, stimulate growth of cartilage-forming cells or induce differentiation of progenitors of cartilage-forming cells and chondrocytes.

The methods and kits of the present invention also provide improved chemically defined medium for accelerating the proliferation of chondrocytes (cartilage-forming cells). In another embodiment, the compositions and methods of the present invention can be used to treat chondrocytic cell lines, such as articular chondrocytes, in order to maintain chondrocytic phenotype and survival of the cells. The treated cell populations are therefore also useful for gene therapy applications.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen (Clouston et al., *Genomics* 2:240–248 (1988); Kageyama et al, *Biochemistry* 23:3603–3609; Ohkubo et al., *Proc. Natl. Acad. Sci.* 80:2196–2200 (1983); each reference hereby incorporated in its entirety). The substance so formed is a decapeptide called angiotensin I (AII) which is converted to AII by the angiotensin converting enzyme (ACE) which removes the C-terminal His-Leu residues from AI [SEQ ID NO: 37]. AII is a known pressor agent and is commercially available.

Studies have shown that AII increases mitogenesis and chemotaxis in cultured cells that are involved in wound repair, and also increases their release of growth factors and extracellular matrices (dizerega, U.S. Pat. No. 5,015,629; Dzau et. al., *J. Mol. Cell. Cardiol.* 21:S7 (Supp III) 1989; Berk et. al., *Hypertension* 13:305–14 (1989); Kawahara, et al., *BBRC* 150:52–9 (1983); Naftilan, et al., *J. Clin. Invest.* 83:1419–23 (1989); Taubman et al., *J. Biol. Chem.* 264:526–530 (1989); Nakahara, et al., *BBRC* 184:811–8 (1992); Stouffer and Owens, *Circ. Res.* 70:820 (1992); Wolf, et al., *Am. J. Pathol.* 140:95–107 (1992); Bell and Madri, *Am. J. Pathol.* 137:7–12 (1990). In addition, AII was shown to be angiogenic in rabbit corneal eye and chick chorioallantoic membrane models (Fernandez, et al., *J. Lab. Clin. Med.* 105:141 (1985); LeNoble, et al., Eur. J. Pharmacol. 195:305–6 (1991). Additionally, AII and angiotensin III analogs and fragments thereof have been shown to be effective in wound healing. (U.S. Pat. No. 5,629,292; International Application No. WO 95/08565; International Application WO 95/08337; International Application No. WO 96/39164; all references hereby incorporated in their entirety.)

Previous studies have suggested that angiotensin I (AI) and AII both stimulate bone resorption in vitro by osteoclasts incubated on bone slices, but only in the presence of osteoblastic cells, suggesting that the effect of angiotensin II was not direct, but rather is mediated by a primary hormonal interaction on cells of the osteoblastic lineage. (Hatton et al., *J. Endocrinol.* 152:5–10 (1997)). AI stimulation of bone resorption was inhibited by ACE inhibitors, suggesting that the formation of AII from AI was responsible for the stimulation of bone resorption. Neither AI nor AII were shown to have any effect on osteoclast formation. Thus, this study suggests that local bone destruction may be mediated by AII's stimulation of bone resorption.

Other studies have demonstrated AII stimulation of DNA and collagen synthesis in vitro on primary cultures of isolated, phenotypically immature osteoblasts derived from the periosteum of fetal rat calvaraiae and human adult trabecular bone. (Lamparter et al., *J. Cell. Physiol.* 175:89–98 (1998)) No direct AII effect was detected on primary cell populations with a mature osteoblast phenotype, and an indirect effect through AII-responsive osteoblastic precursor cells was proposed. Similar in vitro studies on osteoblast-rich populations of cells demonstrated a similar effect, while not ruling out stimulation of mature osteoblast proliferation. (Hiruma et al., *Biochem and Biophys. Res. Commun.* 230:176–178 (1997)) Another study suggests that AII may decelerate the differentiation and bone formation of rat calvarial osteoblasts. (Hagiwara et al., J. of Endocrinology 156:543–550 (1998))

Based on all of the above studies, there is no expectation that the use of angiotensinogen, angiotensin I (AI), AI analogues, AI fragments and analogues thereof, AII, AII analogues, AII fragments or analogues thereof or AII $AT_2$ type 2 receptor agonists would be effective in enhancing bone and cartilage repair, or effective in accelerating chondrocyte proliferation and collagen synthesis.

Previous studies in our laboratory have demonstrated that a class of AII and AII analogues and fragments stimulate the proliferation of mesenchymal stem cells, which give rise to the cells that make up bone and cartilage. (U.S. patent application Ser. No. 09/012,400, filed Jan. 23, 1998, herein incorporated by reference in its entirety.)

A peptide agonist selective for the AT2 receptor (AII has 100 times higher affinity for AT2 than ATI) has been identified. This peptide is p-aminophenylalanine 6-AII ["(p-NH$_2$-Phe)6-AII)"], Asp-Arg-Val-Tyr-Ile-Xaa-Pro-Phe [SEQ ID NO.36] wherein Xaa is p-NH$_2$-Phe (Speth and Kim, BBRC 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The effects of AII receptor and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffman, et al., *Life Sci.* 49:223–228 (1991); Viswanathan, et al., *Peptides* 13:783–786 (1992); Kimura, et al., *BBRC* 187:1083–1090 (1992).

Many studies have focused upon AII1(1-7) (AII residues 1-7) or other fragments of AII to evaluate their activity. AII(1-7) elicits some, but not the full range of effects elicited by AII. Pfeilschifter, et al., *Eur. J Pharmacol.* 225:57–62 (1992); Jaiswal, et al., *Hypertension* 19(Supp. II):II-49-II-55 (1992); Edwards and Stack, *J. Pharmacol. Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Poitsi, et a., *Br. J Pharmacol.* 111:652–654 (1994).

As hereinafter defined, a preferred class of AT2 agonists for use in accordance with the present invention comprises angiotensinogen, angiotensin I (AI), AI analogues, AI fragments and analogues thereof, AII, AII analogues, AII fragments or analogues thereof or AII AT$_2$ type 2 receptor agonists having p-NH-Phe in a position corresponding to a position 6 of AII. In addition to peptide agents, various nonpeptidic agents (e.g., peptidomimetics) having the, requisite AT2 agonist activity are further contemplated for use in accordance with the present invention.

The active AII analogues, fragments of AII and analogues thereof of particular interest in accordance with the present invention comprise a sequence consisting of at least three contiguous amino acids of groups $R^1$–$R^8$ in the sequence of general formula I $$R^1\text{-}R^2\text{-}R^3\text{-}R^4\text{-}R^5\text{-}R^6\text{-}R^7\text{-}R^8$$

in which $R^1$ and $R^2$ together form a group of formula

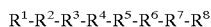
$$X\text{—}R^A\text{—}R^B\text{—},$$

wherein X is H or a one to three peptide group, or is absent, $R^A$ is suitably selected from H, Asp, Glu, Asn, Acpc (1-aminocyclopentane carboxylic acid), Ala, Me$^2$Gly, Pro, Bet, Glu(NH$_2$), Gly, Asp(NH$_2$) and Suc, $R^B$ is suitably selected from Arg, Lys, Ala, Orn, Citron, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO$_3$)$_2$, Thr, Ala, Ser, homoSer and azaTyr;

$R^5$ is selected from the group consisting of Ile, Ala, Leu, norLeu, Val and Gly;

$R^6$ is His, Arg or 6-NH$_2$-Phe;

$R^7$ is Pro or Ala; and $R^8$ is selected from the group consisting of Phe, Phe(Br), Ile and Tyr, excluding sequences including $R^4$ as a terminal Tyr group, or is absent.

Compounds falling within the category of AT2 agonists useful in the practice of the invention include the AII analogues set forth above subject to the restriction that $R^6$ is p-NH$_2$-Phe.

Particularly preferred combinations for $R^A$ and $R^B$ are Asp-Arg, Asp-Lys, Glu-Arg and Glu-Lys. Particularly preferred embodiments of this class include the following: AII, AIII or AII(2-8), Arg-Val-Tyr-Ile-His-Pro-Phe [SEQ ID NO:2]; AII(3-8), also known as desI-AIII or AIV, Val-Tyr-Ile-His-Pro-Phe [SEQ ID NO:3]; AII(1-7), Asp-Arg-Val-Tyr-Ile-His-Pro {SEQ ID NO:4]; AII(2-7). Arg-Val-Tyr-Ile-His-Pro [SEQ ID NO:5]; AII(3-7), Val-Tyr-Ile-His-Pro [SEQ ID NO:6]; AII(5-8), Ile-His-Pro-Phe [SEQ ID NO:7]; AII(1-6), Asp-Arg-Val-Tyr-Ile-His [SEQ ID NO:8]; AII(1-5), Asp-Arg-Val-Tyr-Ile [SEQ ID NO:9]; AII(1-4), Asp-Arg-Val-Tyr [SEQ ID NO:10]; and AII(1-3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6-8), His-Pro-Phe [SEQ ID NO:14] and AII(4-8), Tyr-Ile-His-Pro-Phe [SEQ ID NO:15] were also tested and found not to be effective.

In a particularly preferred embodiment of the methods for chondrocyte proliferation, collagen synthesis, cartilage repair, and attachment and fixation of cartilage to bone or other tissues, the active compounds of the present invention are selected from those comprising the following general formula:

R1-R2-R3-R4-R5-His-Pro-R6, wherein

R1 is selected from the group consisting of Hydrogen, Gly, and Asp;

R2 is selected from the group consisting of Arg, Citron, or Ornithine;

R3 is selected from the group consisting of Val, Ile, Ala, Leu, and norLeu, or Pro;

R4 is selected from Tyr, Tyr(PO$_3$)$_2$, and Ala;

R5 is selected from the group consisting of Ile, Ala, Val, Leu, and norLeu; and

R6 is Phe, Ile, or is absent.

Most particularly preferred embodiments of this class of compounds are selected from the group consisting of SEQ ID NO:1, SEQ ID NO:2, SEQ ID NO:4, SEQ ID NO: 13, SEQ ID NO: 18, SEQ ID NO:19, SEQ ID NO:12, SEQ ID NO:24, SEQ ID NO:26, SEQ ID NO: 32, SEQ ID NO:33, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

In a particularly preferred embodiment of the methods for bone repair and bone and prosthesis implantation, the active compounds of the present invention are selected from those comprising the following general formula:

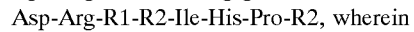
Asp-Arg-R1-R2-Ile-His-Pro-R2, wherein

R1 is selected from the group consisting of Ile, Pro, Ala, Val, Leu, and norLeu;

R2 is selected from Tyr and Tyr(PO$_3$)$_2$; and

R3 is Phe, or is absent.

Most particularly preferred embodiments of this class of compounds are selected from the group consisting of SEQ ID NO:1, SEQ ID NO:4, SEQ ID NO:24, SEQ ID NO:31, SEQ ID NO:32, SEQ ID NO: 33, SEQ ID NO:41, and SEQ ID NO: 45.

Another class of compounds of particular interest in accordance with the present invention are those of the general formula II

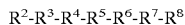

in which $R^2$ is selected from the group consisting of H, Arg, Lys, Ala, Orn, Citron, Ser(Ac), Sar, D-Arg and D-Lys;

$R^3$ is selected from the group consisting of Val, Ala, Leu, norLeu, Ile, Gly, Pro., Aib, Acpc and Tyr;

$R^4$ is selected from the group consisting of Tyr, Tyr($PO_3$)$_2$, Thr, Ser, homoSer., Ala, and azaTyr;

$R^5$ is selected from the group consisting of Ile, Ala, Leu, norLeu, Val and Gly;

$R^6$ is His, Arg or 6-$NH_2$-Phe;

$R^7$ is Pro or Ala; and $R^8$ is selected from the group consisting of Phe, Phe(Br), Ile and Tyr.

A particularly preferred subclass of the compounds of general formula II has the formula $R^2$-$R^3$-Tyr-$R^5$-His-Pro-Phe [SEQ ID NO:16]

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4-8) was ineffective in repeated tests; this is believed to be due to the exposed tyrosine on the N-terminus.

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |
| Orn | Ornithine |

It has been suggested that AII and its analogues adopt either a gamma or a beta turn (Regoli, et al., *Pharmacological Reviews* 26:69 (1974). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, norLeu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr ($PO_3$)$_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). $R^3$ may also be suitably Ala.

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, Gly and Val.

In the angiotensinogen, AI, AI analogues, AI fragments and analogues thereof, AII analogues, fragments and analogues of fragments of particular interest in accordance with the present invention, $R^6$ is His, Arg or 6-$NH_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogues of interest to receptors; therefore, Tyr and especially Phe are preferred for purposes of the present invention.

Analogues of particular interest include the following:

TABLE 2

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID |

TABLE 2-continued

Angiotensin II Analogues

| AII Analogue Name | Amino Acid Sequence | Sequence Identifier |
|---|---|---|
| Analogue 9 | Asp-Arg-Val-Tyr-Ile-Arg-Pro-Phe | SEQ ID NO: 26 |
| Analogue 10 | Asp-Arg-Val-Tyr-Ile-His-Ala-Phe | SEQ ID NO: 27 |
| Analogue 11 | Asp-Arg-Val-Tyr-Ile-His-Pro-Tyr | SEQ ID NO: 28 |
| Analogue 12 | Pro-Arg-Val-Tyr-Ile-His-Pro-Phe | SEQ ID NO: 29 |
| Analogue 13 | Asp-Arg-Pro-Tyr-Ile-His-Pro-Phe | SEQ ID NO: 30 |
| Analogue 14 | Asp-Arg-Val-Tyr(PO$_3$)$_2$-Ile-His-Pro-Phe | SEQ ID NO: 31 |
| Analogue 15 | Asp-Arg-norLeu-Tyr-Ile-His-Pro-Phe | SEQ ID NO: 32 |
| Analogue 16 | Asp-Arg-Val-Tyr-norLeu-His-Pro-Phe | SEQ ID NO: 33 |
| Analogue 17 | Asp-Arg-Val-homoSer-Tyr-Ile-His-Pro-Phe | SEQ ID NO: 34 |
|  |  | SEQ ID NO: 35 |

The polypeptides of the instant invention may be synthesized by any conventional method, including, but not limited to, those set forth in J. M. Stewart and J. D. Young, *Solid Phase Peptide Synthesis,* 2nd ed., Pierce Chemical Co., Rockford, Ill. (1984) and J. Meienhofer, *Hormonal Proteins and Peptides,* Vol. 2, Academic Press, New York, (1973) for solid phase synthesis and E. Schroder and K. Lubke, *The Peptides,* Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert sol id support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

In one aspect, the present invention provides methods and kits for enhancing bone and cartilage repair, implantation, and augmentation in a mammal comprising the administration of angiotensinogen, angiotensin I (AI), AI analogues, AI fragments and analogues thereof, angiotensin II (AII), AII analogues, AII fragments or analogues thereof or AII AT$_2$ type 2 receptor agonists (hereinafter referred to as "active agents"). The compounds can be administered alone or in combination with other compounds that enhance bone and/ or cartilage repair, implantation, and augmentation, including but not limited to bone morphogenic protein-2, bone morphogenic protein-4, bone morphogenic protein-6, bone morphogenic protein-7, transforming growth factor-beta, insulin-like growth factor, and parathyroid hormone.

The active agents may be administered by any suitable route, including orally, parentally, by inhalation spray, rectally, or topically in dosage unit formulations containing conventional pharmaceutically acceptable carriers, adjuvants, and vehicles. Such vehicles may include a tantalum or hydroxyapatite scaffold as a vehicle with the compounds of the invention embedded therein. Alternatively, polymeric substrates can be used for compound delivery to the bone or cartilage such as the polymeric substrates disclosed in U.S. Pat. Nos. 5,443,515; 5,171,273; 5,607,474; 4,916,207; and 5,324,775; all references hereby incorporated in their entirety. The term parenteral as used herein includes topical (i.e.: placement in to the bone), subcutaneous, intravenous, intraarterial, intramuscular, intrasternal, intratendinous, intraspinal, intracranial, intrathoracic, infusion techniques or intraperitoneally.

The active agents of the present invention can also be incorporated into a coating on the surface of a prosthetic device. Such coatings may be composed of a polymer that allows slow diffusion of the active agents at a rate sufficient to enhance bone attachment for a suitable period of time. Suitable coatings include, but are not limited to, hydroxyapatite, methacrylate and tricalcium phosphate. Further, the polymeric coatings can be applied only to the sites on the prosthetic device where bony ingrowth is desired. Bone grafts can be coated with or soaked or immersed in a rinse or gel prior to implantation so as to impregnate the graft with the active agents. Topical or local administration of the active agents to either the site of implantation or the implant itself, is preferred, as it diminishes drug exposure for tissues and organs not requiring treatment.

The active agents may be made up in a solid form (including granules, powders or suppositories) or in a liquid form (e.g., solutions, suspensions, or emulsions). The compounds of the invention may be applied in a variety of solutions. Suitable solutions for use in accordance with the invention are sterile, dissolve sufficient amounts of the peptide, and are not harmful for the proposed application. In this regard, the compounds of the present invention are very stable but are hydrolyzed by strong acids and bases. The compounds of the present invention are soluble in organic solvents and in aqueous solutions at pH 5-8.

The active agents may be subjected to conventional pharmaceutical operations such as sterilization and/or may contain conventional adjuvants, such as preservatives, stabilizers, wetting agents, emulsifiers, buffers etc.

For administration, the active agents are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Formulations suitable for topical administration include liquid or semi-liquid preparations suitable for penetration through the skin (e.g., liniments, lotions, ointments, creams, or pastes) and drops suitable for administration to the eye, ear, or nose.

The dosage regimen for enhancing bone and cartilage repair with the active agents is based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods. Dosage levels of the order of between 0.1 ng/kg and 10 mg/kg body weight of the active agents are useful for all methods of use disclosed herein.

As an example, the dosage regimen for accelerating bone and cartilage repair with the active agents wherein the compounds are embedded in a scaffold used for bone and/or cartilage, such as tantalum or hydroxyappetite, would be based upon the volume of bone to be filled and not upon the weight of the subject being treated. Following determination of the specific dose volume to be administered to the subject, calculated based on the defect, individual doses are prepared. The final delivered drug product will be mixed under aseptic conditions at a ratio of: 1 part (20%) of the active agents (in a concentration of between about 0.001 $\mu$g/ml to about 5 mg/ml) to 4 parts (80%) diluent.

The treatment regime will also vary depending on the disease being treated, based on a variety of factors, including the type of injury, the age, weight, sex, medical condition of the individual, the severity of the condition, the route of administration, and the particular compound employed. For example, the active agents are administered to an osteoporosis patient for up to 30 days. The therapy is administered for 1 to 6 times per day at dosages as described above.

In a preferred embodiment, the active agent is administered subcutaneously. A suitable subcutaneous dose of active ingredient of active agent is preferably between about 0.1 ng/kg and about 10 mg/kg administered twice daily for a time sufficient to enhance bone or cartilage repair. In a more preferred embodiment, the concentration of active agent is between about 100 ng/kg body weight and about 10.0 mg/kg body weight. In a most preferred embodiment, the concentration of active agent is between about 10 $\mu$g/kg body weight and about 10.0 mg/kg body weight. This dosage regimen maximizes the therapeutic benefits of the subject invention while minimizing the amount of agonist needed. Such an application minimizes costs as well as possible deleterious side effects.

For subcutaneous administration, the active ingredient may comprise from 0.0001% to 10% w/w, e.g., from 1% to 2% by weight of the formulation, although it may comprise as much as 10% w/w, but preferably not more than 5% w/w, and more preferably from 0.1% to 1% of the formulation.

In another preferred embodiment of the present invention, the active agent is administered topically at the site of bone or cartilage loss or repair. Suitable topical doses and active ingredient concentration in the formulation are as described for subcutaneous administration.

In another preferred embodiment, the active agent is administered at the desired site of bone or cartilage repair, such as via capsule delivery in gingival tissue at sites of bone resorption or in a scaffold surgically implanted at the site of a non-union bone fracture. Suitable doses and active ingredient concentration in the formulation are as described for subcutaneous administration.

In one embodiment of the invention, ex vivo methods are presented for enhancing bone repair via isolation of osteoblastic cell populations from a subject, contacting the isolated cell population with angiotensinogen, AI, AI analogues, AI fragments and analogues thereof, AII, AII analogues, AII fragments and analogues thereof and/or AII $AT_2$ type 2 receptor agonist, and subsequent reinfusion of the osteoblastic cell population into the subject. Methods for the isolation of osteoblastic cell population have been described. (Hiruma et al., 1997; Lamparter et al., 1998) In a preferred embodiment, human bone cells are cultured from outgrowths of trabecular bone fragments of the femoral head from patients undergoing hip replacement due to fracture, and treated by several consecutive collagenase digestion periods, using 1 mg/ml type II collagenase solution (Worthington Diagnostic Systems) for 20 minutes per digestion period.

In another embodiment of the invention, ex vivo or in vitro methods are presented for enhancing cartilage repair via isolation of chondrocyte cell populations from a subject, contacting the isolated cell population with the active agent, and subsequent reinfusion of the chondrocyte cell population into the subject. Methods for the isolation of chondrocyte cell populations have been described. (Kato et al., J. Cell Biol., vol. 100, pages 477–485 (1985); U.S. Pat. Nos. 4,642,120; 5,053,050; and 5,736,372, each herein incorporated by reference in its entirety).

In a preferred embodiment, autologous or homologous bone marrow is obtained by aspiration with a bone biopsy needle from the iliac crest or femoral canal. (U.S. Pat. No. 5,053,050) The aspirated cells are injected into a phosphate buffered saline (PBS) containing 0.25% trypsin and injected sequentially through 17, 18 and 20 gauge needles to achieve a single cell suspension. The cells are plated in a density of 50–100×10$^6$ cells on 100 mm tissue culture dishes fed with BGJ b medium (GIBCO) with 15% F.C.S. (Fetal Calf Serum). The medium is changed daily or as required by the proliferation rate of the cells. The medium is supplemented with between about 0.1 ng/ml and 10 mg/ml active agent. The cells are subcultured weekly and after 5-6 subculturings an almost pure fibroblastic stromal cell population is achieved. This cell population is then trypsinized and put in a suspension culture at a density of 3–8×10$^6$ cells/ml of medium and cultured above soft agar in a F-12 medium with 10% F.C.S. and 50 $\mu$g/ml sodium ascorbate added daily to the medium. The fibroblastic stromal cells start to aggregate immediately and after three-seven days most of the cells are in aggregates of 30–60 cells. All the aggregates express a chondrogenic phenotype, as determined by employing histochemical and immunohistochemical probes for analysis.

Although bone marrow derived chondrocytes are preferred, chondrocytes of autologous or homologous origin, or homologous committed chondrocytes, or any other progenital cells of mesenchymal origin can be used. It can be seen that this initial formulation comprises purification, proliferation and manipulation of a population expressing a chondrogenic phenotype. More specifically, the proliferating cells are from the class comprising bone marrow stroma cells, embryonal committed chondrocytes and any undifferentiated mesenchymal cells.

In a preferred embodiment, the proliferative effect of the active agents of the invention on cartilage cells is assessed by reactivity to an antibody directed against a protein known to be present in higher concentrations in proliferating cells than in non-proliferating cells, including but not limited to proliferating cell nuclear antigen (PCNA, or cyclin; Zymed Laboratories, South San Francisco, Calif.). Viable cells may also be identified using a technique such as the trypan blue exclusion assay. Cells to be reinfused into the subject are rinsed to remove all traces of culture fluid, resuspended in an appropriate medium and then pelleted and rinsed several times. After the final rinse, the cells are resuspended at between 0.7×10⁶ and 50×10⁶ cells per ml in an appropriate medium and administered as described below.

Alternatively, the effects of the active agents on matrix component synthesis in bone and cartilage cells are determined in organ culture and in isolated cells by measuring the levels of two matrix proteins, as described in U.S. Pat. No. 5,686,116 incorporated by reference herein in its entirety. Type I collagen is the major matrix protein of bone and cartilage. Collagen is almost entirely composed of proline, OH-proline, alanine and glycine. Thus, new-bone collagen synthesis can be determined by measuring the uptake of $^3$H-Pro or by following the appearance of $^3$H-OH-Pro, which is formed by conversion of proline subsequent to its incorporation into collagen. Osteocalcin is a bone-specific matrix protein which is thought to be a cell signal for attracting osteoclasts to bone to initiate bone breakdown, and is also thought to slow or impede formation of newly mineralizing bone. Price et al., Proc. Natl. Acad. Sci. USA, 79:7734–7738 (1982). Therefore, decreased osteocalcin synthesis is associated with bone repair.

Any synoviocyte (cartilage-forming) cells can be used. In a preferred embodiment, the cell line HIG-82, a permanent cartilage cell line which retains many features present in normal synoviocytes, is used. Georgescu et al., In Vitro Cell. Dev. Biol., 24:1015–1022 (1988).

The synoviocytes are exposed to active agent for 24–48 hours, after which total cellular RNA is isolated by standard means. (*Molecular Cloning: A Laboratory Manual* (Sambrook, el al., 1989, Cold Spring Harbor Laboratory Press)) Detection of mRNA for type I collagen can be performed via standard techniques in the art including but not limited to reverse transcription-polymerase chain reaction (RT-PCR) using primers specific to type I collagen or osteocalcin, or Northern blotting of the RNA followed by hybridization with probes for type I collagen or osteocalcin. (*Molecular Cloning: A Laboratory Manual* (Sambrook, et al., 1989, Cold Spring Harbor Laboratory Press).

Alternatively, the expression of type I collagen synthesis is determined in organ culture as described in U.S. Pat. No. 5,686,116. In a preferred embodiment, calvarial (skull) bones from newborn rats are placed in sterile culture dishes with a nutritive media to maintain viability. In this state, structural tissues grow by forming new matrix components (notably bone-specific collagen), but this growth is very slow. Kream et al., Endocrinol., 116:296–302 (1985). Hemicalvaria from 21 day old fetal rats are incubated for 48 hours in the presence and absence of angiotensinogen, AI, AI analogues, AI fragments and analogues thereof, AII, AII analogues, AII fragments and analogues thereof and/or AII $AT_2$ type 2 receptor agonist at various concentrations. $^3$H-Pro is added for the final 18 hours of the incubation. Results showing that AII increases the levels of proline (Pro) and hydroxyproline (OH-Pro) in fetal rat hemicalvaria demonstrate that AII can increase the level of type I collagen synthesis in a normal bone culture system.

In another embodiment, the present invention comprises a method to enhance bone or cartilage repair in vivo by administration of the active agents of the invention. In one embodiment, the compounds of the invention are injected into the subcutaneous tissue over the right calvarium of mice. Control vehicle is PBS supplemented with 1% BSA. Heparin is administered at a dose of 50 units/mi. The animals are sacrificed on day 14 and bone growth is measured by histomorphometry.

Bone samples for quantitation are cleaned from adjacent tissues and fixed in 10% buffered formalin for 24–48 hours, decalcified in 14% EDTA for 1–3 weeks, processed through graded alcohols and embedded in paraffin wax. Three micron sections of the calvaria and femurs are prepared. Representative sections are selected for histomorphometric assessment of the effects of the active agent on bone formation and bone resorption. Sections are measured by using a camera attachment to directly trace the microscopic image onto a digitizing plate. Bone changes are measured on sections collected 200 mu m apart, over 4 adjacent 1×1 mm fields on both the injected and noninjected sides of the calvaria. New bone is identified by its woven, rather than lamellar structure, and osteoclasts and osteoblasts are identified by their distinctive morphology. Histomorphometry software (Osteomeasure, Osteometrix, Inc., Atlanta) is used to process digitizer input to determine cell counts and feature areas or perimeters.

Alternatively, the active agents of the invention can be used to potentiate osteoblast function in intact animals. In a preferred embodiment, a model for abnormal osteoblast activity, weanling Sprague-Dawley rats, are placed on a phosphate and vitamin D-deficient diet as per the manufacturer's instructions (the diet, #80039, Teklad, Madison, Wis.) The animals on the diet are also kept in the dark to prevent de novo vitamin D synthesis. Animals placed under such conditions show abnormal bone formation and a marked deficiency in total bone mass.

One group of the weanling rats on the diet is treated with active agent at between about 0.1 ng/kg and 10 mg/kg, given as a subcutaneous injection, every other day for 21 days. One group on the diet remains untreated and served as the control. Littennate controls not on the diet and not treated with active agent supply blood samples at the time of sacrifice of the animals on the diet for determination of alkaline phosphatase activity. Upon sacrifice, the long bones are removed from the animals on the diet for subsequent analyses.

Serum alkaline phosphatase activity is used as a reliable indicator of osteoblast activity, such that increased levels of alkaline phosphatase activity are evidence of the abnormal bone turnover in the experimental animals. Serum alkaline phosphatase activity is determined by measuring the hydrolysis of p-nitrophenyl phosphate by serum samples according to the method of Lowry et al., J. Biol. Chem., 207:19–37 (1954). Markedly elevated serum alkaline phosphatase activity indicates abnormal osteoblast activity. By contrast, normalization of bone cell function is evidenced by a decreased level of serum alkaline phosphate activity and increased bone mass (tested via determination of the ash weight of bones) relative to control animals.

Alternatively, a full thickness articular cartilage defect model in the femoral-patellar joint of adult rabbits is used to evaluate the ability of the compounds of the present invention to affect cartilage and bone repair, as described in U.S. Pat. No. 5,700,774, hereby incorporated by reference in its entirety. Adult New Zealand White rabbits are anesthetized and prepared for sterile surgery. A 3×3 mm defect through articular cartilage and into underlying subchondral bone is drilled into the patellar groove of the knee joint. The defect is either left empty, filled with collagen sponge (controls), or with collagen sponge soaked with between about 0.1 ng/ml and 10 mg/ml active agent. The incision is closed and animals are allowed free movement within their cages for 4 weeks. After 4 weeks the animals are humanely euthanatized and the articular cartilage/subchondral bone defect is evaluated histologically for tissue architecture, quantity and quality of repair tissue. Northern analysis is performed for additional phenotyping.

In a further embodiment, dental and orthopedic implants can be coated with the compounds of the invention. In general, implant devices are coated with the active agents of the invention dissolved at a concentration in the range of 0.1 ng/ml to 10 mg/ml in phosphate-buffered saline (PBS) containing 2 mg/ml serum albumin. The porous end of an implant is dipped in the solution and is air dried (or lyophilized) or implanted immediately into the bony site. The viscosity of the coating solution is increased, if desired, by adding hyaluronate at a final concentration of 0.1 mg/ml to 100 mg/ml or by adding other pharmaceutically acceptable excipients. Alternatively, the solution containing the active agent is mixed with collagen gel or human collagen (e.g. Zyderm Registered TM Collagen Implant, Collagen Corp., Palo Alto, Calif.) to a final collagen concentration of 2 mg/ml to 100 mg/ml to form a paste or gel, which is then used to coat the porous end of the implant device. The coated implant device is placed into the bony site immediately or is air dried and rehydrated with PBS prior to implanting, with the objective of maximizing new bone formation into the implant while minimizing the ingrowth of soft tissue into the implant site.

In a further aspect, the present invention provides kits for enhancing bone or cartilage repair, wherein the kits comprise an effective amount of active agent for bone or cartilage repair, and instructions for using the amount effective of active agent as a therapeutic. In a preferred embodiment, the kit further comprises a pharmaceutically acceptable carrier, such as those adjuvants described above. In another preferred embodiment, the kit further comprises a means for delivery of the active agent to a patient. Such devices include, but are not limited to syringes, matrical or micellar solutions, bandages, wound dressings, polymeric scaffolds, collagen vehicles, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery may either contain the effective amount of the active agent, or may be separate from the compounds, which are then applied to the means for delivery at the time of use.

The kits may further comprise an amount effective for bone and/or cartilage repair, implantation, and augmentation of additional compounds, including but not limited to bone morphogenic protein-2, bone morphogenic protein4, bone morphogenic protein-6, bone morphogenic protein-7, transforming growth factor-beta, insulin-like growth factor, and parathyroid hormone. The kit may optionally contain a pharmaceutically acceptable carrier.

In another aspect of the present invention, an improved cell culture medium is provided for the proliferation of chondrocytes, wherein the improvement comprises addition to the cell culture medium of an effective amount of active agent to stimulate chondrocyte proliferation. Any cell culture media that can support the growth of chondrocytes can be used with the present invention. Such cell culture media include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, Opti-MEM® Reduced-Serum Medium, RPMI Medium, and Macrophage-SFM Medium or combinations thereof.

The improved cell culture medium can be supplied in either a concentrated (ie: 1X) or non-concentrated form, and may be supplied as either a liquid, a powder, or a lyophilizate. The cell culture may be either chemically defined, or may contain a serum supplement. Culture media is commercially available from many sources, such as GIBCO BRL. (Gaithersburg, Md.) and Sigma (St. Louis, Mo.).

In another embodiment, the methods of the present invention can be used to treat chondrocytic cell lines, such as articular chondrocytes, in order to maintain chondrocytic phenotype and survival of the cells. The treated cell populations are therefore also useful for gene therapy applications.

In another preferred embodiment, the kit further comprises a sterile container. The sterile container can comprise either a sealed container, such as a cell culture flask, a roller bottle, or a centrifuge tube, or a non-sealed container, such as a cell culture plate or microtiter plate (Nunc; Naperville, Ill.).

In a further preferred embodiment, the kit further comprises an antibiotic supplement for inclusion in the reconstituted cell growth medium. Examples of appropriate antibiotic supplements include, but are not limited to actimonycin D, Fungizone®, kanamycin, neomycin, nystatin, penicillin, streptomycin, or combinations thereof (GIBCO).

A further object of the present invention is to provide pharmaceutical compositions comprising the active agents as an ingredient for use in the methods of the invention. The compositions comprise the active agents together with a compound or compounds that also enhance bone or cartilage implantation, repair and regeneration, including, but not limited to bone morphogenic protein-2, bone morphogenic protein-4, bone morphogenic protein-6, bone morphogenic protein-7, transforming growth factor-beta, insulin-like growth factor, and parathyroid hormone, together with a pharmaceutically acceptable carrier, this term including any carrier which does not interfere with the effectiveness of the biological activity of the active agents and other compounds, and which is not toxic to the host to which it is administered. Dosage and administration of the pharmaceutical compositions will vary depending on the disease being treated, based on a variety of factors, including the type of injury, the age, weight, sex, medical condition of the individual, the severity of the condition, the route of administration, and the particular compound employed, as above. Thus, the dosage regimen may vary widely, but can be determined routinely by a physician using standard methods.

The present invention fulfills the need for methods to enhance bone and cartilage repair in a mammal suffering from a wide variety of disorders and injuries including, but not limited to bone fractures, defects, and disorders which result in weakened bones such as osteoporosis, osteoarthritis, Paget's disease, osteohalisteresis, osteomalacia, periodontal disease; bone loss resulting from multiple myeloma and other forms of cancer; bone loss resulting from side effects of other medical treatment (such as steroids); age-related loss of bone mass; articular cartilage tears, deformities and other cartilage defects such as arthritis and cartilaginous tissue damage.

Example 1. Method for Culture of Rabbit Chondrocytes

Chondrocytes were isolated from the cartilage of the knee joints of adult rabbits and cultured according to the method of Okazaki et al. (Ann. Rheum. Dis. 55:181–186, 1996). Briefly, cartilage explants were minced into small pieces (approximately 1.5 mm by 1.5 mm). The tissue pieces were digested at 37° C. sequentially in 0.05% hyaluronidase (415 U/mg protein) for 10 minutes, 0.2% Type III trypsin (10,000 U/mg protein, Sigma) and 0.53 mM EDTA for 15 minutes, and 0.2% Type I collagenase (136 U/mg protein, Sigma) for 30 minutes. The samples were then washed and incubated overnight at 37° C. in 5% $CO_2$ in air in Dulbecco's modified Eagle's medium enriched with 10% fetal calf serum, 3.5 mg/ml glucose, 0.2% Type I collagenase and antibiotics (100 U/ml penicillin and 100 μg/ml streptomycin).

Figure 2:
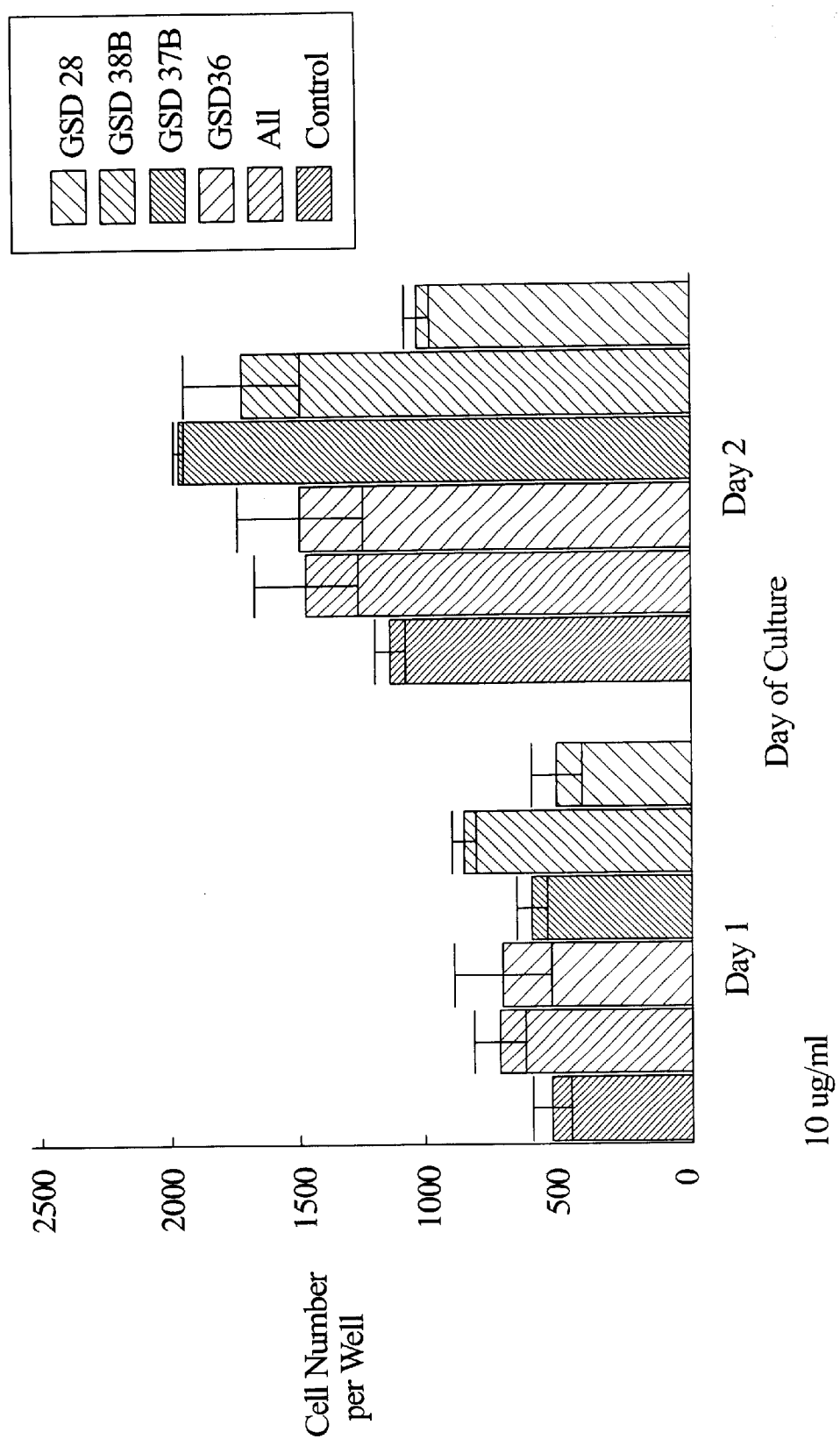
FIG. 2 is a bar graph showing the effect of AII, GSD36, GSD37B, GSD38B, and GSD28 (10 μg/ml) of the invention on chondrocyte proliferation.
Figure 3:
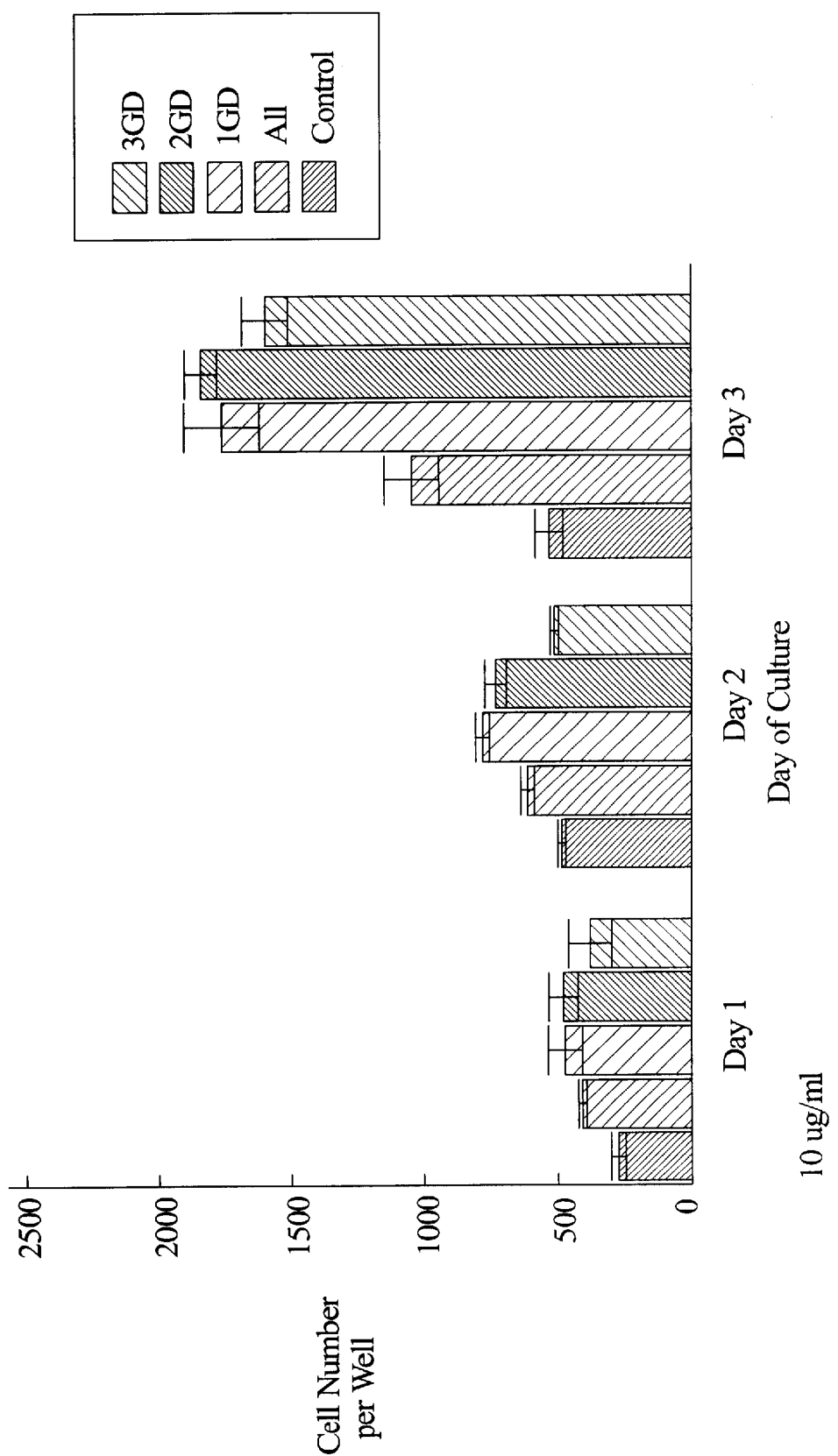
FIG. 3 is a bar graph showing the effect of AII, 1GD, 2GD, and 3GD (10 μg/ml) on chondrocyte proliferation.
Figure 4:
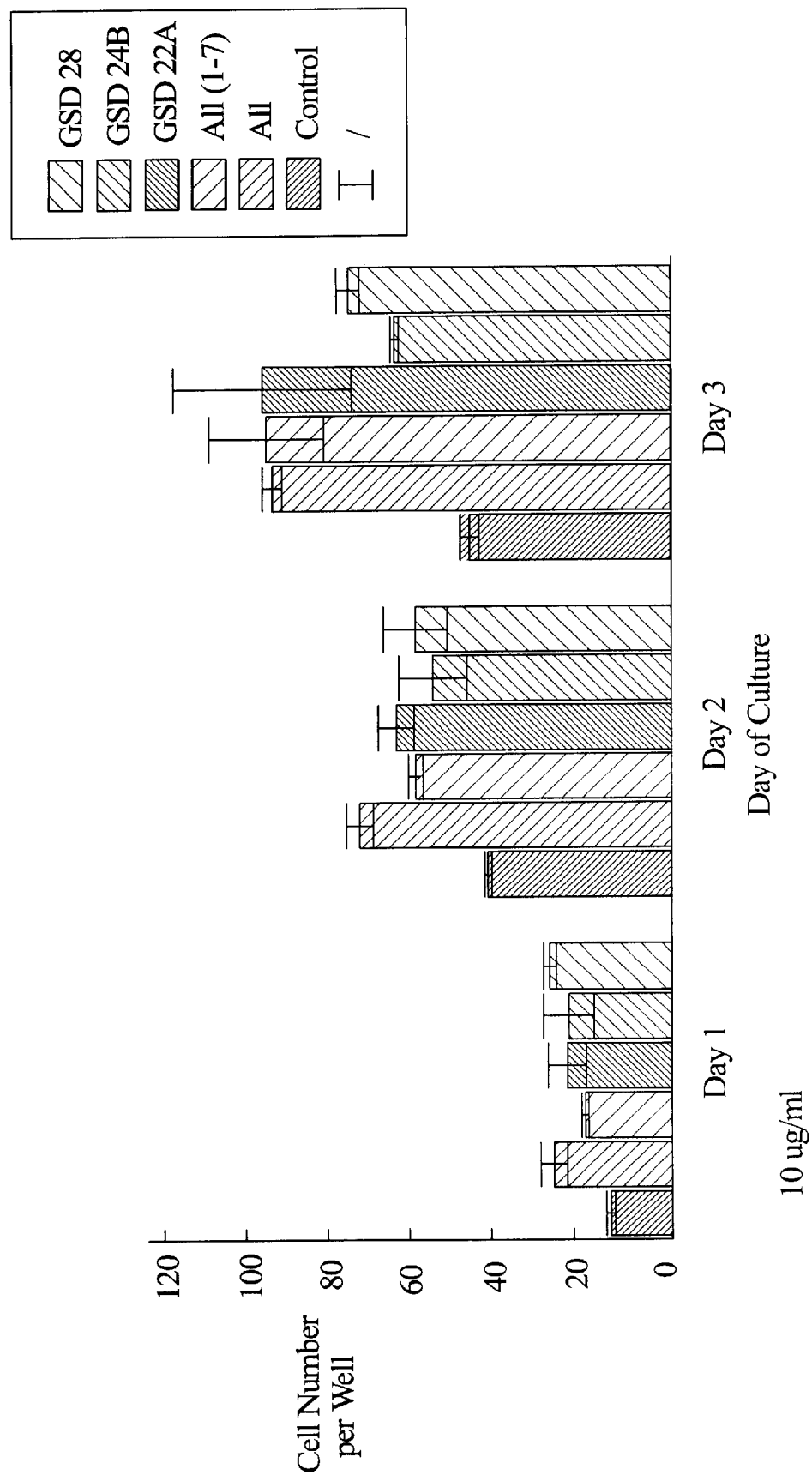
FIG. 4 is a bar graph showing the effect of AII, AII(1-7), GSD22A, GSD24B, and GSD28 (10 μg/ml) of the invention on chondrocyte proliferation.

After this incubation, the cells were harvested and washed once with phosphate buffered saline (pH 7.2). The cells were then counted with a hemacytometer and resuspended at $1 \times 10^5$ cells/ml in Ham's F12 supplemented with 10% fetal calf serum and antibiotics. A 10 ml aliquot of cells was transferred to collagen coated 25 cm$^2$ flasks (coated with collagen isolated from rat tail tendons) and incubated at 37° C. in 5% $CO_2$ in air. Five to seven days after the initiation of culture, the cells were detached with 0.05% trypsin-EDTA (Gibco-BRL) at 37° C. in 5% $CO_2$ in air. After detachment, the cells were washed once with phosphate buffered saline, centrifuged and resuspended at 200 cells/ml in Ham's F12 supplemented with 10% fetal calf serum and antibiotics. Two hundred microliters of cells were then aliquoted into the collagen coated wells of a 96 well microtiter plate and allowed to adhere, after which, 10 μg/ml of the AII and AII analogue and fragment peptides listed in Table 3 were added to the wells to assess their effects on chondrocyte proliferation on days 1, 2, and 3 after culture initiation. Cell numbers were quantitated by staining the cells with Giemsa stain and counting the number of nuclei detected via microscopy. The data (FIGS. 1–4) demonstrate that AII and the AII analogues and fragments all accelerated the chondrocyte proliferation.

TABLE 3

Designation for Analogues/Fragments Used in Example 1

| Name | Abbreviation | Sequence | SEQ ID NO: |
|---|---|---|---|
| GSD 37B | Orn$^2$-AII | D(Orn)VYIHPF | SEQ ID NO: 38 |
| GSD 28 | Ile$^8$-AII | DRVYIHPI | SEQ ID NO: 39 |
| GSD 24B | Pro$^3$-AII | DRPYIHPF | SEQ ID NO: 31 |
| GSD 22A | Ala$^4$-AIII | RVYAHPF | SEQ ID NO: 18 |
| GSD 36 | Gly$^1$-AII | GRVYIHPF | SEQ ID NO: 42 |
| GSD 38B | Citron$^2$-AII | D(Citron)VYIHPF | SEQ ID NO: 43 |
| 1GD | Ala$^4$-AII(1–7) | DRVAIHP | SEQ ID NO: 40 |
| 2GD | Pro$^3$-AII(1–7) | DRPYIHP | SEQ ID NO: 41 |
| 3GD | Pro$^3$Ala$^4$-AII(1–7) | DRPAIHP | SEQ ID NO: 44 |
| AIII | AII(2–8) | RVYIHPF | SEQ ID NO: 2 |
| AII(1–7) | | DRVYIHP | SEQ ID NO: 4 |
| AII | | DRVYIHPF | SEQ ID NO. 1 |

Example 2. Bone Healing

Female, Sprague Dawley rats underwent intramuscular anesthesia with ketamine/rompum and were prepared for sterile surgery by shaving the surgical site and scrubbing with Betadine scrub followed by 70% ethanol. The rat was then placed on a sterile field in a lateral decubitis position facing the surgeon. The shaved legs were then covered with Betadine solution and draped aseptically. A skin incision was performed parallel to the long axis of the right medial diaphysis. The muscle was separated along fascial planes to expose the tibia. A defect of 1.4 mm in diameter was then drilled from the lateral side of the midshaft cortex so that the defect extended from one cortical side to the other, through the bone marrow. Sterile saline (0.9% NaCl) for injection was then used to clean the surgical area of tissue debris and bone fragments. Either hydron polymer solution (vehicle: 10% Hydron, 60% ethanol, 1% polyethylene glycol polymer) or peptide (AII, AII(1-7), or 9 GD at 1 mg/ml) in hydron polymer solution was placed in the bone defect to fill the defect with polymer (approximately 0.1 ml of polymer). The incision was closed with 3-0 Vicryl suture using continuous mattress suture. The animals were allowed to recover from anesthesia, given Bupronex for analgesia and allowed free movement, until euthanasia 7 days later.

By gross observation, the defects that received the peptides of the invention were more completely filled with new tissue that had begun to calcify. The majority of control defects were less than 50% filled with new tissue and no hardening of the tissue was observed. These data demonstrate that the peptides of the invention accelerate the formation of new bone tissue.

After gross evaluation, the muscle tissue was removed from the bone and the bones were placed in formalin for fixation. After 2 days in 10% buffered formaldehyde, the tissues were placed in a decalcifying solution (Rapid Bone Decal, American MasterTech Scientific, Inc. Lodi, Calif.) diluted 3:1 for 6 hours. After decalcification, the bone was cut in half along the long axis, embedded in paraffin, sectioned and stained with hematoxylin and eosin.

Microscopic evaluation of the tissue sections confirmed the gross observations. On day 7, the bones in which the defect had been filled with Hydron (the placebo) had a loose fibrin filler with the majority of cells observed being inflammatory in nature. Occasionally, a cell that appeared to be of mesenchymal origin or a blood vessels was seen at the site of injury. In all of the peptide treated animals, extensive stromal cell ingrowth with numerous blood vessels was observed. In approximately 50% of the peptide treated animals, tissue with the appearance of new bone was observed. These data clearly support the ability of these angiotensin peptides to accelerate new bone formation.

TABLE 4

Designation for Analogues/Fragments used in Example 2

| AII(1–7) | | DRVYIHP | SEQ ID NO: 4 |
|---|---|---|---|
| AII | | DRVYIHPF | SEQ ID NO. 1 |
| 9GD: | NorLeu3-AII(1–7) | DR(nor)YIHP | SEQ ID NO: 45 |

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the full scope of the appended claims.

We claim:

1. A method for enhancing bone repair in a mammal, comprising the administration of an amount effective for enhancing bone repair in the mammal of at least one active agent comprising a sequence of at least three contiguous amino acids of groups $R^1$–$R^8$ in the sequence of general formula I $$R^1\text{-}R^2\text{-}R^3\text{-}R^4\text{-}R^5\text{-}R^6\text{-}R^7\text{-}R^8$$

wherein $R^1$ is selected from H, Asp, Glu, Asn, Acpc (1-aminocyclopentane carboxylic acid), Ala, $Me^2Gly$, Pro, Bet, $Glu(NH_2)$, Gly, $Asp(NH_2)$ and Suc, $R^2$ is selected from Arg, Lys, Ala, Orn, Citron, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, $Tyr(PO_3)_2$, Thr, Ala, Ser, homoSer and azaTyr;

$R^5$ is selected from the group consisting of Ile, Ala, Leu, norLeu, Val and Gly;

$R^6$ is selected from the group consisting of His, Arg or 6-$NH_2$-Phe;

$R^7$ is selected from the group consisting of Pro or Ala; and $R^8$ is selected from the group consisting of Phe, Phe(Br), Ile and Tyr;

excluding sequences including $R^4$ as a terminal Tyr group, or is absent.

2. The method of claim 1 wherein the active agent comprises an amino acid sequence selected from the group consisting of angiotensinogen, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

3. The method of claim 1 further comprising administration of an amount effective for enhancing bone repair in the mammal of at least one compound selected from bone morphogenic protein-2, bone morphogenic protein4, bone morphogenic protein-6, bone morphogenic protein-7, transforming growth factor-beta, insulin-like growth factor, and parathyroid hormone.

4. An improved method for bone and prosthesis implantation in a mammal, comprising the administration of an amount effective for enhancing bone and prosthesis implantation in the mammal of at least one active agent comprising a sequence of at least three contiguous amino acids of groups $R^1$–$R^8$ in the sequence of general formula I $$R^1\text{-}R^2\text{-}R^3\text{-}R^4\text{-}R^5\text{-}R^6\text{-}R^7\text{-}R^8$$

wherein $R^1$ is selected from H, Asp, Glu, Asn, Acpc (1-aminocyclopentane carboxylic acid), Ala, $Me^2Gly$, Pro, Bet, $Glu(NH_2)$, Gly, $Asp(NH_2)$, and Suc R² is selected from Arg, Lys, Ala, Orn, Citron, Ser(Ac), Sar, D-Arg and D-Lys;

R³ is selected from the group consisting of Val, Ala, Leu, norLeu, Ile, Gly, Pro, Aib, Acpc and Tyr;

R⁴ is selected from the group consisting of Tyr, Tyr(PO₃)₂, Thr, Ala, Ser; homoSer and azaTyr;

R⁵ is selected from the group consisting of Ile, Ala, Leu, norLeu, Val and Gly;

R⁶ is selected from the group consisting of His, Arg or 6-NH₂-Phe;

R⁷ is selected from the group consisting of Pro or Ala; and

R⁸ is selected from the group consisting of Phe, Phe(Br), Ile and Tyr;

excluding sequences including R⁴ as a terminal Tyr group, or is absent.

5. The method of claim 4 wherein the active agent comprises an amino acid sequence selected from the group consisting of angiotensinogen, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

6. The method of claim 4 further comprising administration of an amount effective for enhancing bone and prosthesis implantation in the mammal of at least one compound selected from bone morphogenic protein-2, bone morphogenic protein-4, bone morphogenic protein-6, bone morphogenic protein-7, transforming growth factor-beta, insulin-like growth factor, and parathyroid hormone.

7. A kit for enhancing bone repair in a mammal, comprising:

(a) administering an amount effective for enhancing bone repair in the mammal of at least one active agent comprising a sequence comprising a sequence of at least three contiguous amino acids of groups R¹–R⁸ in the sequence of general formula I

R¹-R²-R³-R⁴-R⁵-R⁶-R⁷-R⁸ wherein R¹ is selected from H, Asp, Glu, Asn, Acpc (1-aminocyclopentane carboxylic acid), Ala, Me²Gly, Pro, Bet, Glu(NH₂), Gly, Asp(NH₂) and Suc, R¹ is selected from Arg, Lys, Ala, Om, Citron, Ser(Ac), Sar, D-Arg and D-Lys;

R³ is selected from the group consisting of Val, Ala, Leu, norLeu, Ile, Gly, Pro, Aib, Acpc and Tyr;

R⁴ is selected from the group consisting of Tyr, Tyr(PO₃)₂, Thr, Ala, Ser; homoSer and azaTyr;

R⁵ is selected from the group consisting of Ile, Ala, Leu, norLeu, Val and Gly;

R⁶ is selected from the group consisting of His, Arg or 6-NH₂-Phe;

R⁷ is selected from the group consisting of Pro or Ala; and

R⁸ is selected from the group consisting of Phe, Phe(Br), Ile and Tyr; excluding sequences including R⁴ as a terminal Tyr group, or is absent; and (b) instructions for using the amount effective of active agent to enhance bone repair in a mammal.

8. The kit of claim 7 wherein the active agent comprises an amino acid sequence selected from the group consisting of angiotensinogen, SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

9. The kit of claim 7 further comprising an amount effective for enhancing bone repair in the mammal of at least one compound selected from bone morphogenic protein-2, bone morphogenic protein-4, bone morphogenic protein-6, bone morphogenic protein-7, transforming growth factor-beta, insulin-like growth factor, and parathyroid hormone.

10. The kit of claim 7 further comprising a means for delivery of the active agent.

11. A method for enhancing cartilage repair in a mammal, comprising the administration of an amount effective to enhance cartilage repair to the mammal of at least one active agent comprising a sequence of at least three contiguous amino acids of groups R¹–R⁸ in the sequence of general formula I

R¹-R²-R³-R⁴-R⁵-R⁶-R⁷-R⁸ wherein R¹ is selected from H, Asp, Glu, Asn, Acpc (1-aminocyclopentane carboxylic acid), Ala, Me²Gly, Pro, Bet, Glu(NH₂), Gly, Asp(NH₂) and Suc, R² is selected from Arg, Lys, Ala, Orn, Citron, Ser(Ac), Sar, D-Arg and D-Lys;

R³ is selected from the group consisting of Val, Ala, Leu, norLeu, Ile, Gly, Pro, Aib, Acpc and Tyr;

R⁴ is selected from the group consisting of Tyr, Tyr(PO₃)₂, Thr, Ala, Ser; homoSer and azaTyr;

R⁵ is selected from the group consisting of Ile, Ala, Leu, norLeu, Val and Gly;

R⁶ is selected from the group consisting of His, Arg or 6-NH₂-Phe;

R⁷ is selected from the group consisting of Pro or Ala; and

R⁸ is selected from the group consisting of Phe, Phe(Br), Ile and Tyr;

excluding sequences including R⁴ as a terminal Tyr group, or is absent.

12. The method of claim 11 wherein the active agent comprises an amino acid sequence selected from the group consisting of angiotensinogen, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

13. An improved method for attachment and fixation of cartilage implants to bone or other tissue in a mammal, comprising the administration of an amount effective for attaching and fixing cartilage implants to bone or other tissue in a mammal of at least one active agent comprising a sequence of at least three contiguous amino acids of groups $R^1$–$R^8$ in the sequence of general formula I

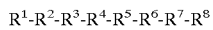

wherein $R^1$ is selected from H, Asp, Glu, Asn, Acpc (1-aminocyclopentane carboxylic acid), Ala, Me²Gly, Pro, Bet, Glu(NH₂), Gly, Asp(NH₂) and Suc, $R^2$ is selected from Arg, Lys, Ala, Orn, Citron, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO₃)₂, Thr, Ala, Ser, homoSer and azaTyr;

$R^5$ is selected from the group consisting of Ile, Ala, Leu, norLeu, Val and Gly;

$R^6$ is selected from the group consisting of His, Arg or 6-NH₂-Phe;

$R^7$ is selected from the group consisting of Pro or Ala; and $R^8$ is selected from the group consisting of Phe, Phe(Br), Ile and Tyr;

excluding sequences including $R^4$ as a terminal Tyr group, or is absent.

14. The method of claim 13 wherein the active agent comprises an amino acid sequence selected from the group consisting of angiotensinogen, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

15. An improved medium for the culture of chondrocytes wherein the improvement comprises contacting the cells with an amount effective to accelerate proliferation of chondrocytes of at least one active agent comprising a sequence of at least three contiguous amino acids of groups $R^1$–$R^8$ in the sequence of general formula I

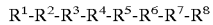

wherein $R^1$ is selected from H, Asp, Glu, Asn, Acpc (1-aminocyclopentane carboxylic acid), Ala, Me²Gly, Pro, Bet, Glu(NH₂), Gly, Asp(NH₂) and Suc, $R^2$ is selected from Arg, Lys, Ala, Orn, Citron, Ser(Ac), Sar, D-Arg and D-Lys;

$R^3$ is selected from the group consisting of Val, Ala, Leu, norLeu, Ile, Gly, Pro, Aib, Acpc and Tyr, $R^4$ is selected from the group consisting of Tyr, Tyr(PO₃)₂, Thr, Ala, Ser, homoSer and azaTyr;

$R^5$ is selected from the group consisting of Ile, Ala, Leu, norLeu, Val and Gly;

$R^6$ is selected from the group consisting of His, Arg or 6-NH₂-Phe;

$R^7$ is selected from the group consisting of Pro or Ala; and $R^8$ is selected from the group consisting of Phe, Phe(Br), Ile and Tyr; excluding sequences including $R^4$ as a terminal Tyr group, or is absent.

16. The improved chemically defined medium of claim 15 wherein the active agent comprises an amino acid sequence selected from the group consisting of angiotensinogen, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

17. A method for enhancing bone repair in a mammal, comprising the administration of an amount effective for enhancing bone repair in the mammal of at least one active agent of the formula Asp-Arg-R1-R2-Ile-His-Pro-R2, wherein R1 is selected from the group consisting of Ile, Pro, Ala, Val, Leu, and norLeu;

R2 is selected from Tyr and Tyr(PO₃)₂; and

R3 is Phe, or is absent.

18. The method of claim 17 wherein the active agent comprises an amino acid sequence selected from the group consisting of SEQ ID NO:1, SEQ ID NO:4, SEQ ID NO:24, SEQ ID NO:31, SEQ ID NO:32, SEQ ID NO: 33, SEQ ID NO:41, and SEQ ID NO: 45.

19. The method of claim 17 further comprising the administration of an amount effective for enhancing bone repair in the mammal of at least one compound selected from bone morphogenic protein-2, bone morphogenic protein-4, bone morphogenic protein-6, bone morphogenic protein-7, transforming growth factor-beta, insulin-like growth factor, and parathyroid hormone.

20. An improved method for bone and prosthesis implantation in a mammal, comprising the administration of an amount effective for enhancing bone and prosthesis implantation to the mammal of at least one active agent of the formula Asp-Arg-R1I-2-Ile-His-Pro-R2, wherein R1 is selected from the group consisting of Ile, Pro, Ala, Val, Leu, and norLeu;

R2 is selected from Tyr and Tyr(PO3)₂; and

R3 is Phe, or is absent.

21. The method of claim 20 wherein the active agent comprises an amino acid sequence selected from the group consisting of SEQ ID NO:1, SEQ ID NO:4, SEQ ID NO:24, SEQ ID NO:31, SEQ ID NO:32,SEQ ID NO:33,SEQ ID NO:41, and SEQ ID NO:45.

22. The method of claim 20 further comprising the administration of an amount effective for enhancing bone repair in the mammal of at least one compound selected from bone morphogenic protein-2, bone morphogenic protein-4, bone morphogenic protein-6, bone morphogenic protein-7, transforming growth factor-beta, insulin-like growth factor, and parathyroid hormone.

23. A method for enhancing cartilage repair in a mammal, comprising the administration of an amount effective to enhance cartilage repair to the mammal of at least one active agent of the formula R1-R2-R3-R4-R5-His-Pro-R6, wherein R1 is selected from the group consisting of Hydrogen, Gly, and Asp;

R2 is selected from the group consisting of Arg, Citron, or Ornithine;

R3 is selected from the group consisting of Val, Ile, Ala, Leu, and norLeu, or Pro;

R4 is selected from Tyr, Tyr(PO$_3$)$_2$, and Ala;

R5 is selected from the group consisting of Ile, Ala, Val, Leu, and norLeu; and

R6 is Phe, Ile, or is absent.

24. An improved method for attachment and fixation of cartilage implants to bone or other tissue in a mammal, comprising the administration of an amount effective for attaching and fixing cartilage implants to bone or other tissue in a mammal of at least one active agent of the formula R1-R2-R3-R4-R5-His-Pro-R6, wherein R1 is selected from the group consisting of Hydrogen, Gly, and Asp;

R2 is selected from the group consisting of Arg, Citron, or Ornithine;

R3 is selected from the group consisting of Val, Ile, Ala, Leu, and norLeu, or Pro;

R4 is selected from Tyr, Tyr(PO$_3$)$_2$, and Ala;

R5 is selected from the group consisting of Ile, Ala, Val, Leu, and norLeu; and

R6 is Phe, Ile, or is absent.

25. A pharmaceutical composition comprising (a) an amount effective to enhance bone repair or bone and prosthesis implantation in a mammal of at least one active agent comprising a sequence of the formula Asp-Arg-R1-R2-Ile-His-Pro-R2, wherein R1 is selected from the group consisting of Ile, Pro, Ala, Val, Leu, and norLeu;

R2 is selected from Tyr and Tyr(PO$_3$)$_2$; and

R3 is Phe, or is absent; and (b) an amount effective to enhance bone repair or bone and prosthesis implantation in a mammal of at least one compound selected from bone morphogenic protein-2, bone morphogenic protein-4, bone morphogenic protein-6, bone morphogenic protein-7, transforming growth factor-beta, insulin-like growth factor, and parathyroid hormone; and (c) a pharmaceutically acceptable carrier.

26. A pharmaceutical composition comprising (a) an amount effective to enhance bone repair or bone and prosthesis implantation in a mammal of at least one active agent comprising a sequence consisting of at least three contiguous amino acids of groups R$^1$–R$^8$ in the sequence of general formula I

R$^1$-R$^2$-R$^3$-R$^4$-R$^5$-R$^6$-R$^7$-R$^8$ in which R$^1$ and R$^2$ together form a group of formula

X—R$^A$—R$^B$—, wherein X is H or a one to three peptide group, or is absent,

R$^A$ is suitably selected from H, Asp, Glu, Asn, Acpc (1-aminocyclopentane carboxylic acid), Ala, Me$^2$Gly, Pro, Bet, Glu(NH$_2$), Gly, Asp(NH$_2$) and Suc, R$^B$ is suitably selected from Arg, Lys, Ala, Om, Citron, Ser(Ac), Sar, D-Arg and D-Lys;

R$^3$ is selected from the group consisting of Val, Ala, Leu, norLeu, Ile, Gly, Pro, Aib, Acpc and Tyr;

R$^4$ is selected from the group consisting of Tyr, Tyr(PO$_3$)$_2$, Thr, Ala, Ser, homoSer and azaTyr;

R$^5$ is selected from the group consisting of Ile, Ala, Leu, norLeu, Val and Gly;

R$^6$ is His, Arg or 6-NH$_2$-Phe;

R$^7$ is Pro or Ala; and

R$^8$ is selected from the group consisting of Phe, Phe(Br), Ile and Tyr, excluding sequences including R$^4$ as a terminal Tyr group, or is absent;

(b) an amount effective to enhance bone repair or bone and prosthesis implantation in a mammal of at least one compound selected from bone morphogenic protein-2, bone morphogenic protein-4, bone morphogenic protein-6, bone morphogenic protein-7, transforming growth factor-beta, insulin-like growth factor, and parathyroid hormone; and (c) a pharmaceutically acceptable carrier.

27. The method of any one of claims 1, 4, 15 or 19 wherein the active agent comprises at least four contiguous amino acids of general formula I.

28. The method of any one of claims 1, 4, 15 or 19 wherein the active agent comprises at least five contiguous amino acids of general formula I.

29. The method of any one of claims 1, 4, 15 or 19 wherein the active agent comprises at least six contiguous amino acids of general formula I.

30. The method of any one of claims 1, 4, 15 or 19 wherein the active agent comprises at least seven contiguous amino acids of general formula I.

31. The method of any one of claims 1, 4, 15 or 19 wherein the active agent consists of at least three contiguous amino acids of general formula I.

32. The method of any one of claims 1, 4, 11 or 13 wherein the active agent consists of at least four contiguous amino acids of general formula I.

33. The method of any one of claims 1, 4, 11 or 13 wherein the active agent consists of at least five contiguous amino acids of general formula I.

34. The method of any one of claims 1, 4, 11 or 13 wherein the active agent consists of at least six contiguous amino acids of general formula I.

35. The method of any one of claims 1, 4, 11 or 13 wherein the active agent consists of at least seven contiguous amino acids of general formula I.

* * * * *